(12) United States Patent  
Barker et al.

(10) Patent No.: US 9,097,618 B2  
(45) Date of Patent: Aug. 4, 2015

(54) METHOD FOR PREPARING CELL STANDARD

(75) Inventors: Craig Barker, Whitely Bay (GB); Victoria Reid, Newcastle Upon Tyne (GB)

(73) Assignee: LEICA BIOSYSTEMS NEWCASTLE LIMITED, Newcastle Upon Tyne (GB)

( * ) Notice: Subject to any disclaimer, the term of this patent is extended or adjusted under 35 U.S.C. 154(b) by 646 days.

(21) Appl. No.: 13/054,785

(22) PCT Filed: Jul. 17, 2009

(86) PCT No.: PCT/IB2009/006253  
§ 371 (c)(1), (2), (4) Date: Apr. 21, 2011

(87) PCT Pub. No.: WO2010/007509  
PCT Pub. Date: Jan. 21, 2010

(65) Prior Publication Data  
US 2011/0189722 A1    Aug. 4, 2011

Related U.S. Application Data

(60) Provisional application No. 61/081,962, filed on Jul. 18, 2008.

(30) Foreign Application Priority Data

Jul. 18, 2008    (AU) ................................ 2008903692

(51) Int. Cl.  
*G01N 1/06* (2006.01)  
*G01N 1/31* (2006.01)

(52) U.S. Cl.  
CPC . *G01N 1/06* (2013.01); *G01N 1/312* (2013.01)

(58) Field of Classification Search  
CPC .............................................. G01N 33/57415  
See application file for complete search history.

(56) References Cited

U.S. PATENT DOCUMENTS

| | | |
|---|---|---|
| 4,820,504 A | 4/1989 | Battifora |
| 6,387,653 B1 | 5/2002 | Voneiff et al. |
| 6,411,434 B1 | 6/2002 | Eastman et al. |
| 7,374,907 B1 | 5/2008 | Voneiff et al. |
| 2003/0059851 A1 | 3/2003 | Smith |
| 2004/0126837 A1 | 7/2004 | Baker |
| 2007/0070357 A1 | 3/2007 | Aiyer |

FOREIGN PATENT DOCUMENTS

| | | |
|---|---|---|
| EP | 0 121 340 A2 | 10/1984 |
| EP | 0 345 953 A2 | 12/1989 |
| EP | 1 739 388 A1 | 1/2007 |
| EP | 1985985 | 10/2008 |
| JP | 2007/212388 | 8/2007 |
| WO | WO 99/44062 A1 | 9/1999 |
| WO | WO 2008/066846 | 6/2008 |
| WO | WO 2008/066846 A2 | 6/2008 |
| WO | WO 2010/007509 A1 | 1/2010 |

OTHER PUBLICATIONS

Rhodes et al., "A Formalin-Fixed, Paraffin-Processed Cell Line Standard for Quality Control of Immunohistolchemical Assay of HER-2/neu Expression in Breast Cancer", Am. J. Clin. Pathol. 117 : 81-89 (2002).*  
Hallen, "Quantitative Analysis of Sectioned Biological Material", J. Histochem. and Cytochem. 10 (1) : 96-101 (1962).*  
Anthony et al., "Interferometric analysis of intrasection and intersection thickness variability associated with cryostat microtomy", Histochemical J. 16 : 61-70 (1984).*  
EPO Communication, mailed on Dec. 22, 2011, 7 pages.  
Walker et al., "HER2 testing in the UK: further update to recommendations," J. Clin. Pathol., Jul. 2008, pp. 818-824, vol. 61(7).  
Gown, "Current issues in ER and HER2 testing by IHC in breast cancer," Modern Pathology, (2008) 21, S8-S15.  
Ziebarth, "Fibre-optic focus-detection system for non-contact, high-resolution thickness measurement of transparent tissues," Journal of Physics D. Applied Physics, IOP Publishing, Bristol, GB, vol. 38, No. 15, Aug. 7, 2005, pp. 2708-2715.

* cited by examiner

*Primary Examiner* — Jon P Weber  
*Assistant Examiner* — Teresa E Knight  
(74) *Attorney, Agent, or Firm* — Davis Wright Tremaine LLP

(57) ABSTRACT

The present invention relates to a method for preparing cell samples for histological examination and, more particularly, a method for preparing a cell sample as a standard, or control, for use in the fields of cytology and histology.

15 Claims, 2 Drawing Sheets

METHOD FOR PREPARING CELL STANDARD

CROSS-REFERENCE TO RELATED APPLICATIONS

The present application is a U.S. National Stage entry under 35 U.S.C. §371 of International Application No. PCT/IB2009/006253, filed Jul. 17, 2009, designating the United States of America and published in English on Jan. 21, 2010, which in turn claims priority to U.S. Provisional Patent Application No. 61/081,962 and Australian Patent Application No. 2008903692, both filed on Jul. 18, 2008, each of which is incorporated herein by reference in its entirety.

FIELD OF INVENTION

The present invention relates to a method for preparing cell samples for histological examination and, more particularly, a method for preparing a cell sample as a standard, or control, for use in the fields of cytology and histology. In particular, the invention is related to the fields of immunohistochemistry and molecular cytogenetics.

BACKGROUND OF INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Histology is the study of groups of specialised cells called tissues that are found in most multi-cellular plants and animals. Histological investigation includes study of tissue disease and regeneration and the reaction of tissue to injury or invading organisms. Because normal tissue has a characteristic appearance, histologic examination, such as by immunohistochemistry (IHC) and in situ hybridisation (ISH) is often utilised to identify diseased tissue and tissue morphology.

IHC and ISH both seek to detect a detectable entity in a sample by using specific binding agents capable of binding to the detectable entity. In IHC the specific binding agent generally comprises an antibody, and the detectable entity comprises a polypeptide, protein, or epitope comprised therein. ISH generally comprises detection of a target nucleic acid (such as DNA or RNA) in a sample, via the use of a specific labelled binding agent or probe such as a nucleic acid probe. Both IHC and ISH are routinely used to assist in the differential diagnosis of diseased and normal tissue such as in breast cancer diagnosis.

Evaluation of histological analysis based on visual estimation of the intensity of staining is often imprecise due to a variety of problems that may arise during the assay procedure. This analysis can be greatly improved by the use of appropriate control slides. In a clinical setting, the use of controls, such as positive and negative controls in IHC and ISH is essential.

Controls may be generated, for example, from a characterized archival tissue block or from cell lines embedded in a tissue support medium. In IHC, positive control testing is performed on sections of tissue known to contain the target antigen, processed using the same fixation, epitope retrieval and immunostaining protocols as the patient tissue. A separate tissue section may be used as a positive control, but test sections often contain normal elements that express the antigen of interest (internal controls).

A negative reagent control may be used to assess non-specific staining in patient tissue. A separate section of patient tissue is processed using the same reagent and epitope retrieval protocol as the patient test slide, except that the primary antibody is omitted, and replaced by any of the following: an unrelated antibody of the same isotype as the primary antibody (for monoclonal primary antibodies); an unrelated antibody from the same animal species as the primary antibody (for polyclonal primary antibodies); or the negative control reagent included in the staining kit. A separate negative reagent control should be run for each block of patient tissue being immunostained.

Negative tissue controls are tissues known not to express the antigen of interest, and as such should show no staining if the staining assay is functioning correctly. However, in both positive and negative controls, since the tissue used is non-standardized, it is never fully characterized and so there is always some doubt as to the control's usefulness.

IHC and ISH techniques require a series of treatment steps conducted on a tissue section mounted on a glass slide or other planar support to highlight by selective staining certain morphological indicators of disease states. Thus, for example in IHC, a sample is taken from an individual, fixed and exposed to antibodies against the antigen of interest. Further processing steps, for example, antigen retrieval, exposure to secondary antibodies (usually coupled to a suitable enzyme), washing, and to chromogenic enzyme substrates, etc may be necessary to reveal the pattern of antigen binding.

However, although it is possible with such kits to establish the reference levels of staining, there exists considerable difficulty in establishing a consistent quality of staining of the samples themselves. This arises from a variety of different factors, including non-homogeneous tissue material, the laborious and complex nature of the procedures, variability in reagent quality (including antibody/probe affinity and specificity), the technique of the operator sectioning the material and the subjective nature of the interpretation carried out by the practitioner. Furthermore, other sources of variability in sample staining include the conditions under which tissue samples are collected, processed and stored, variability in epitope retrieval procedures, and enzyme catalysed chromogen precipitation.

At present, the only method available for performing quality control on cut sections is staining by, for example, immunohistochemistry. Testing in this manner is destructive, as once control slides have been stained; they can no longer be supplied as an unstained product to customers. Further, whilst testing in this manner can indicate the quality of a particular section, it does not provide information as to the quality of all unstained sections, especially since the process of preparing numerous cut sections is considerably variable.

Variability in immunohistochemical staining intensity in control cell lines can be the consequence of an additional number of factors. These include any one of, or combination of, methods employed for cell culture, cell line processing such as length and type of fixation, cell line morphology, the percentage confluence at which cells were harvested, the techniques used to harvest cells (enzymatic or physical) and retrieval conditions used during the immunochemistry protocol.

With an increasing demand for control slides in histology, there is a need for a non-destructive method of manufacturing and identifying suitable control slides which can be reliably stained with minimal variability.

SUMMARY OF INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It is well established that the process used to prepare serial sections from tissue/cell line blocks can lead to the production of sections of varying thicknesses. It has now been found that variability in section thickness correlates with staining variability. In particular, with respect to control cell lines used in HER2 testing, the HER2 2+ control cell line MDA-MB 453 (considered clinically borderline positive for HER2) is the most sensitive to variations in thickness and therefore susceptible to exhibiting a raised staining profile beyond its true histochemical profile. An interferometer may be used to accurately determine the thickness of a sectioned tissue sample and thus identify its suitability or otherwise for use as a standard of comparison (control) in histological examination. The sections may be mounted or applied to a suitable planar support, such as a slide, which can be made of glass, polymer or other suitable material, and sectioned samples having a thickness of a predetermined value, as measured by the interferometer, may be deemed suitable for use as a control.

Thus, in a first aspect, the present invention provides a method of identifying the suitability of a sectioned tissue sample for use as a control sample in histological examination comprising the steps of:
(i) measuring the thickness of said sectioned sample using an interferometer; and
(ii) ascertaining whether the thickness of the sectioned sample falls within a predetermined value range.

Yet another aspect of the invention provides a method of selecting a sectioned tissue sample for use as a control sample in histological examination comprising:
(i) measuring the thickness of said sectioned sample using an interferometer; and
(ii) ascertaining whether the thickness of the sectioned sample falls within a predetermined value range; and
(iii) selecting the sample if it has a thickness within said value range.

In another aspect, the invention relates to a method of preparing a tissue sample for use as a control sample in histological examination comprising the steps of:
(i) mounting a sectioned tissue sample to a planar support;
(ii) measuring the thickness of the sectioned sample using an interferometer;
(iii) selecting the sample for use as a control if the thickness of the sectioned tissue sample falls within a predetermined value range.

The thickness of the sample may typically be about 5 μm or less. In some embodiments of the invention, the predetermined thickness of the sectioned tissue sample is in the range of about 4.2 μm to about 2 μm. In further embodiments, the predetermined thickness range is from about 3.6 μm to about 3.2 μm. In further embodiments of the invention, the predetermined range is about 3.25 μm or less, i.e. the selected sample has a thickness of about 3.25 μm or less, typically between about 3.25-3.22 μm.

In one embodiment, the sectioned sample is a section of cells derived from a cultured cell line or a cell block (including solid tissue as well as a section of cells embedded in a rigid support medium). Advantageously, the sectioned sample is a section of cells derived from a cultured cell line embedded in a rigid support medium. The rigid support medium may typically be paraffin.

In some embodiments, the sectioned tissue sample is for use in IHC examinations. In other embodiments, the sectioned tissue sample is for use in ISH examinations.

In further embodiments the control sample is for use in HER2 (IHC) testing.

In a further aspect, the invention relates to an article for use as a control sample in histological testing, wherein the article comprises a planar support on which is applied or mounted at least one sectioned tissue sample having a predetermined thickness as measured by an interferometer.

In an embodiment of the invention, there is provided an article for use as a control sample in HER2 testing comprising a planar support having on the surface thereof at least one tissue sample, wherein said tissue sample has a predetermined thickness and is selected from the group consisting of 0, 1+, 2+ and 3+ cells.

Suitable exemplary cell lines include: SKBR3, MDA-MB-453, MDA-MB-175, MDA-MB-231, BT-474, BT-549, HS578T, MDA-MB-468, SKOV-3, MCF-7, T47D, and MDA-MB-361.

Further embodiments of the invention provide an article for use as a control sample in HER2 testing comprising a planar support having on the surface thereof 2, 3 or 4 tissue samples of predetermined thickness selected from the group consisting of 0, 1+, 2+ and 3+ cells.

In a further embodiment of the invention, there is provided an article for use as a control sample in HER2 testing comprising a planar support having on the surface thereof at least one tissue sample, wherein said tissue sample is selected from group consisting of:
(a) SKBR-3 cells derived having a thickness of 4.2 μm or less;
(b) MDA-MB 453 cells, having a thickness of 3.6 μm or less;
(c) MDA-MB 175 cells, having a thickness of 3.6 μm or less.

In further embodiments, the article comprises at least two of (a)-(c). In further embodiments, the article comprises all three of (a)-(c), optionally further comprising a MDA-MB231 cells.

Where there are at least two cell lines on the planar support, these are discretely and separately located so that the degree of staining can be identified.

BRIEF DESCRIPTION OF THE DRAWINGS

Other features and advantages of one or more preferred embodiments of the present invention will be readily apparent to one of ordinary skill in the art from the following written description with reference to and, used in conjunction with, the accompanying drawings, in which.

DETAILED DESCRIPTION OF THE INVENTION

Figure 1A:
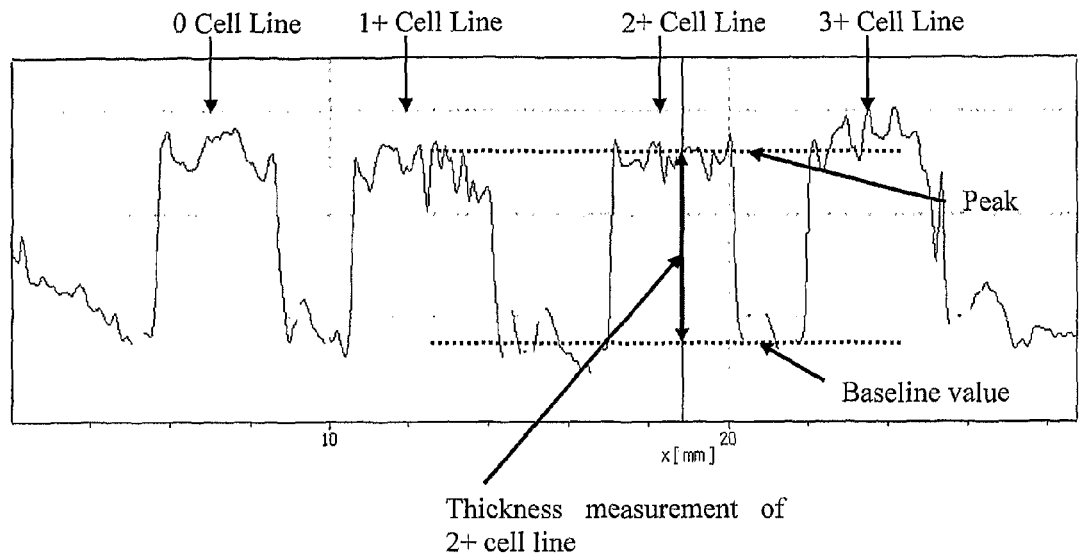
FIG. 1A and FIG. 1B show graphical and 3D images, respectively, of the changes in path length and cell thickness for each cell line.

As used herein, "control" refers to a standard of comparison against which a tissue sample undergoing examination may be compared.

The term "thickness" as used with reference to a sectioned tissue sample refers to the cross sectional profile of said sample. It will be understood that an acceptable thickness of a sectioned sample suitable for use as a control may vary with the nature of the tissue being examined and the particular histological investigation being performed. Suitable thickness value ranges can be determined by one of ordinary skill in the art, for example by correlation of sample thickness with positive assay results to identify optimal or maximum and/or minimum threshold values. Samples which fall within the predetermined value ranges are deemed suitable for the intended use.

It will also be understood that notwithstanding the recitation of a particular thickness value or range of values, there may exist a slight variation in the thickness across a section sample. In particular, a raised profile may be observed towards the outer edge of a section sample, however, this is not included in the thickness determination. In one embodiment, thickness is advantageously measured at or near the core, or central point of the tissue section.

Depending on the nature of the tissue and investigation, a sectioned sample may typically have a thickness of 5 μm or less, such as from about 5 μm down to about 3 μm. or even 2 μm. In further embodiments, the thickness ranges from about 4.2 μm to about 2.5 μm.

In certain embodiments, such as for use in HER-2 assay, depending on the nature of the tissue, the thickness of the sectioned sample is typically from about 4.2 μm or less, or about 3.6 μm or less, for example about 3.25 mm or less, typically from about 3.25 μm to 3.22 μm. Thus, for SKBR-3, the sectional sample is advantageously 4.2 mm or less, for MDA-MB-453 and MDA-MB-175, the sectional sample is advantageously 3.5 μm or less.

The planar support upon which the sectioned tissue sample is mounted, for example a slide, may be of any suitable material, including glass or polymeric material. In typical embodiments, the support is made of glass. In certain embodiments, the sectioned tissue sample is mounted, applied or otherwise fixed to a glass slide using methods known in the art.

The control samples prepared according to the present methods are pre-defined and characterized so that any test results deviating from the expected would indicate a failure with the diagnostic test. For example, a lack of staining or reaction of the control, when it is known to be positive, would indicate a false negative result. Conversely a staining event or reaction in a known negative sample (0+) would indicate a false positive result. The results of the control slide allows one of ordinary skill in the art to evaluate the performance and validity of the diagnostic test and to determine whether the results are acceptable or the test needs to be repeated.

Another use of the control is to compare the intensity or type of result present in the control with that of the test sample. An example of this would be where the a series of control samples have a range of IHC staining intensities present, each sample having a different degree of staining intensity, which can be correlated with a positive or negative result. The patient sample staining intensity is compared to this range and rate of response is determined. The level of intensity is used to diagnose and/or determine prognosis and treatment of the pathology presented. For example, it is well known that in a sub-population of breast cancer patients, if there is found overexpression of the HER-2 protein in the cellular membrane, that is an indication that HERCEPTIN® therapy may be indicated. In HER2 testing, staining profiles are assigned 0, 1+, 2+, or 3+, where 0 and 1+ are considered negative and 2+ and 3+ are considered positive, i.e. the patient may be responsive to HERCEPTIN® treatment.

Interferometry is the technique of using the pattern of interference created by the superposition of two or more waves to diagnose the properties of the aforementioned waves.

Interferometry makes use of the principal of superposition to combine separate waves together in a way that will cause the result of their combination to have some meaningful property that is diagnostic of the original state of the waves. This works because when two waves with the same frequency combine the resulting pattern is determined by the phase difference between the two waves; waves that are in phase will undergo constructive inference while waves that are out of phase will undergo destructive interference.

Typically a single incoming beam of light will be split into two identical beams by a grating or a partial mirror. Each of these beams will travel a different route, called a path, before they are recombined at a detector. The path difference, the difference in the distance traveled by each beam, creates a phase difference between them. It is this introduced phase difference that creates the interference pattern between the initially identical waves. If a single beam has been split along two paths then the phase difference is diagnostic of anything that changes the phase along the paths. This physical change in the path length itself can be used to calculate thickness of the sectioned tissue sample.

In one embodiment, the sectioned sample is a section of cells derived from a cultured cell line or a cell block. In another embodiment, the sectioned sample is a section of cells derived from a cultured cell line embedded in a rigid support medium.

Cell blocks may be prepared from fluid specimens of all types including, but not limited to, effusions, endometrial aspirates, brush samples and fine needle washings.

Advantageously, the sample is a formalin fixed paraffin embedded (FFPE) sample.

It will be understood that the tissue type or cell line employed can be any such tissue or cell line known or used in the art as a standard or control for the particular histological examination. For example, in HER2 testing, reference standards are identified as 0, 1+, 2+ and 3+ (0 and 1+ being negative and 2+ and 3+ being considered positive). The skilled addressee will recognise and understand which tissues/cell lines can be used for the appropriate standard.

Exemplary cell lines which may be used in HER2 testing include, but are not limited to SKBR3, MDA-MB-453, MDA-MB-175, MDA-MB-231, BT-474, BT-549, HS578T, MDA-MB-468, SKOV-3, MCF-7, T47D, and MDA-MB-361. In some embodiments the cell lines are scored as follows: SKBR3 (3+), MDA-MB-453 (2+), MDA-MB-175 (1+), MDA-MB-231 (0), BT-474 (3+), BT-549 (1+), MDA-MB-468 (0), SKOV-3 (3+), MCF-7 (1+), T47D (1+), and MDA-MB-361 (2+).

An acceptable thickness for a 0+ cell line used in HER2 testing samples may be up to about 8.5 μm (as there will be no staining in the negative cell line), but typically 5-2 μm.

An acceptable thickness for the 1+ and 2+ cell lines used in HER2 testing samples may be about 3.6 μm or less, typically 3.5-2.2 μm, such as about 3.5-3.2 μm.

An acceptable thickness for the 3+ cell lines used in HER2 testing samples may be about 4.2 μm or less, typically 4.2-2.5 μm, such as about 3.5-3.2 μm.

In certain embodiments, where multiple cell lines are present (as discrete cores) in a single sectional sample, each cell line sample will be approximately of comparable thickness.

Because the 2+ cell line is considered to be the most sensitive to staining variations due to section thickness, in certain embodiments, particularly where a section from a cell block contains 2, 3 or 4 cell line cores, one of them being a 2+ cell line, it may be sufficient to just measure the thickness of the 2+ sample.

Cell lines have the advantage of uniformity in cell type with no chance of misidentifying the cells. The cell concentration is regulable so that the control slide will have cells evenly distributed and clearly separated. Since the cell line is uniform, the protein digestion conditions may be refined, not merely optimized. Uniformity also reduces interpretation mistakes and permits use of less skilled, and less expensive, personnel. Because cell lines are used, the exact cell type may be used indefinitely as a permanent source of control cells without further need to re-standardize the cell line.

In one embodiment, control slides are prepared by culturing the cell lines, suspending a predetermined concentration of cells in a rigid support medium such as agar, solidifying the agar, formalin fixing, embedding in paraffin, sectioning and mounting on a slide. While these steps are individually well known in the art, numerous variations on the above procedure may be used. For example, other solidifying materials may be used in the place of agar provided that they do not alter the cellular DNA. Examples include plasma, agarose, gelatin, pectin, alginate, carrageenan, monomers, polymers etc. where the gel is formed by cooling, adding ions (e.g. calcium, potassium) adding a polymerizing or a cross linking agent or other fixatives. These solidifying materials, fixatives and cross-linking agents are well known in the art. Paraffin embedding may be standard but other similar materials may be used and may even be optional.

A cell block may comprise a single tissue type or cell line. Alternatively two or more tissue or cell cores may be embedded in a rigid support such that the sectioned material applied to the planar support contains, for example, 2, 3 or 4, tissue types or cell lines.

The slides may also be further processed as required for other examinations of the tissue such as bright field or fluorescent microscopy.

Actual testing conditions include deparaffinization, antigen retrieval or cell conditioning in order to prepare the sample for testing. Diagnostic testing such as IHC and/or ISH is performed on the test sample and the control samples. The testing can be performed manually or on an automated system. The control slide can be run separately but identically to the patient sample, or the patient sample can be mounted onto the same slide as the control and tested together under the same conditions. The results of each sample are then compared using microscopic examination by a person trained in the art of pathology or histology.

The control slide produced according the described methods advantageously may provide reduced staining variability. The control sample also has the advantage of being highly characterized, reproducible and can be manufactured in a routine fashion over time.

As the present invention may be embodied in several forms without departing from the spirit of the essential characteristics of the invention, it should be understood that the above described embodiments are not to limit the present invention unless otherwise specified, but rather should be construed broadly within the spirit and scope of the present invention as defined in the appended claims. Various modifications and equivalent arrangements are intended to be included within the spirit and scope of the present invention and appended claims.

The invention will now be described with reference to the following examples which are intended to illustrate certain embodiments of the invention but are not to be construed as limiting the generality hereinbefore described.

EXAMPLES

Example 1

Preparation of Her 2 Control Slides

The control slides are prepared using the following cell lines:
Negative control cell line MDA-MB-231 (obtained from ECACC—ECACC No. 92020424), positive 1+ control cell line MDA-MB-175-VII (obtained from ATCC—ATCC Catalogue No. HTB-25), positive 2+ control cell line MDA-MB-453 (obtained from ATCC—ATCC Catalogue No. HTB-131) and positive 3+ control cell line SK-BR-3 (obtained from ATCC—ATCC Catalogue No. HTB-30).

Cell lines were obtained from the European Collection of Cell Cultures (ECACC) and the American Type Culture Collection (ATCC)—as detailed in the paragraph above—and grown using standard media and techniques to produce approximately $1-2 \times 10^8$ cells. The cell growth is divided into three batches of approximately $3.3-6.6 \times 10^7$ cells. Cultured cells scraped from the surface of the appropriate number of flasks are spun down and resuspended in formalin and fixed. Each block is paraffin embedded, cut into sections and mounted on a charged glass slide. The HER-2/neu Control Slides were stored at 2° C. to 8° C. after sectioning.

Controls Used in Her-2/Neu Assay

A control slide for an immunohistochemistry Her-2 assay was prepared as a slide containing four cores of control cell lines as described in example 1. The control slides were made by growing the breast carcinoma cell lines using standard laboratory practices. The MDA-MB-231, MDA-MB-175-VII and MDA-MB-453 cells were grown in Leibovitz's medium supplemented with 15% FBS, L-glutamine and antibiotic. MDA-MB-231, MDA-MB-175-VII and MDA-MB-453 cells were maintained under humidified conditions at 37° C. The SK-BR-3 cells were grown in McCoy's 5A medium supplemented with 10% FBS, L-glutamine and antibiotic. SK-BR-3 cells were maintained under humidified conditions containing 5% $CO_2$ at 37° C. Trypsin (0.25%) with EDTA was added to detach adherent cells during subculture. A cell scraper was used to detach adherent cells when harvesting cells for cell block production. Cells were harvested at 60-80% confluence.

The Her-2 control slide allows the user to control for sensitivity and expression level (range of staining intensities), determine treatment (treatment with HERCEPTIN is indicated in cases with a staining intensity greater than 2+), disease prognosis (amplified Her-2 indicates an aggressive carcinoma that is resistant to many treatments) and overstaining (negative sample). If any of the control samples do not stain at the prescribed intensity, those of ordinary skill in the art are alerted to potential misdiagnosis of the patient sample. The type of failure can also be an indication of the source of malfunction in the diagnostic test which facilitates troubleshooting and correction of the malfunction. For example, if the negative sample were to appear positive, this might indicate that there was a rinsing problem with the test or that the incorrect type of test had been used.

Preparation of Quality Control Slides

Embedded control cell lines are cut into sections on a microtome set to 3 microns. Cut sections are then floated out on a water bath and placed onto glass microscope slides.

Slides are then placed in an incubator at 37° C. overnight, followed by a further incubation at 60° C. for 2 hours the next morning, to bake sections onto glass surface and to melt the paraffin wax surroundings the cell spots. Baked slides can then be measured, one by one on the interferometer and the thickness control cell line, relative to the surface of the microscope slide can be measured. Sections are measured using an interferometer device such as the TPM-100 Top Map Metro lab, non-contact interferometer, manufactured by Polytec. When the thickness of the cell spot exceeds the critical threshold of 3.25 microns, slides are considered to have failed and will be discarded. All slides that measure 3.25 microns and under are considered to have passed and can therefore be packaged into batches of 15 slides, together with the liquid componentry of the Oracle Her2 Bond IHC System.

Interferometry

To determine the thickness of the sectioned sample using an interferometer, the slide is placed on a flat, level support at a distance within the field of view of the interferometer. The area of the slide containing the cell lines is identified and marked using the measuring software program of the interferometer. Scanning is commenced and the change in path length between the waves of light is calculated using the measuring software (Polytech, Topography Measurement System V2.1 software).

Figure 1B:
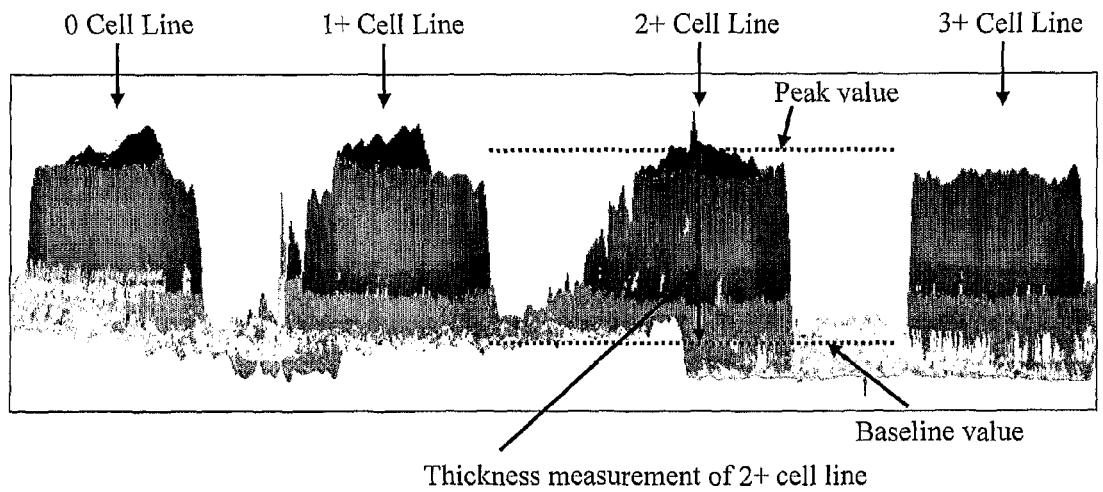
Figure 2A:
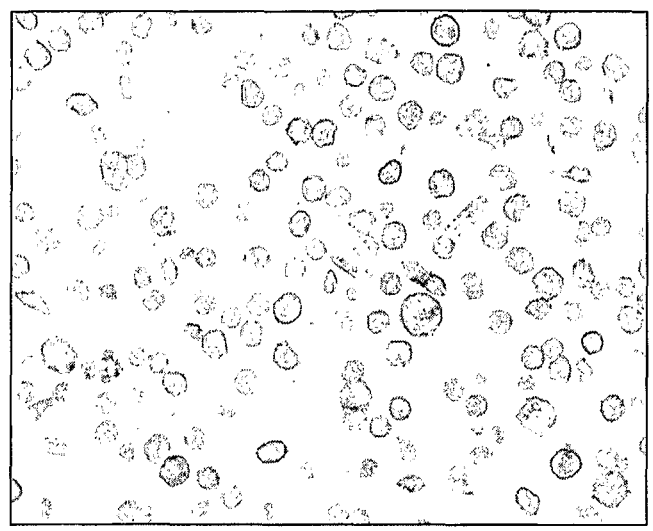
FIG. 2A is a section of MDA-MB-453 segment cut at 3 μm (20× magnification).
Figure 2B:
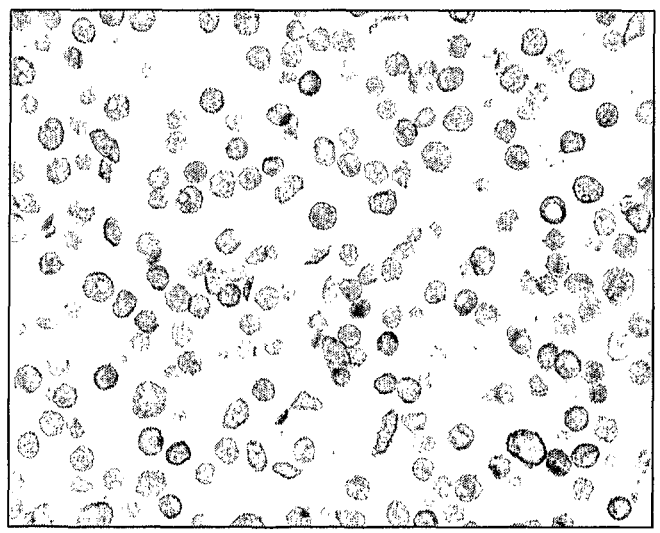
FIG. 2B is an overstained section of MDA-MB-453 segment cut at 5 μm (20× magnification).

The resultant graphical or 3D image representation (see FIGS. 1A and 1B) of the changes in path length, and hence changes in thickness is used to determine the actual thickness of the cell lines relative to the surface of the slide.

Using the method of interferometry, 130 slides containing the SKBR3, MDA-MB-453, MDA-MB-175 and MDA-MB-231 cell lines were assessed. The thickness of each cell line was recorded. Sections were then stained using the Oracle™ HER2 Bond™ IHC System and the HER2 protein expression interpreted as per the Oracle™ HER2 Bond™ IHC System Instructions For Use.

Correlation of thickness and HER2 protein expression for each cell line was performed and from this a critical threshold value, wherein the cross-sectional profile of the sectioned sample applied to the slide was calculated. Slides that measured greater than the critical threshold value were rejected by immunohistochemistry due to over-staining, where those that measured at the critical threshold value or below were identified as acceptable with immunohistochemistry.

The suitability of the critical threshold value was tested in a 'blind fashion' on a subsequent 775 slides containing the SKBr3, MDA-MB-453, MDA-MB-175 and MDA-MB-231 cell lines. One hundred and forty four (144) slides measured above the critical threshold value and these were stained using the Oracle™ HER2 Bond™ IHC System and the HER2 protein expression interpreted as per the Oracle™ HER2 Bond™ IHC System Instructions For Use. Results indicated that 132/144 (91%) would fail to meet the requirements of an Oracle™ HER2 Bond™ IHC System Control and hence would invalidate the test, while 9/144 (9%) would meet the requirement of an Oracle™ HER2 Bond™ IHC System Control and would be considered as wastage in the production procedure. We concluded therefore that our critical threshold was appropriate since of those slides rejected, 91% would also have been rejected following unacceptable IHC staining. Moreover, additional testing (n=8) of every 75th section, from the 631 sections that passed interferometer testing (i.e. measured thickness was below critical threshold) yielded acceptable IHC staining results, indicating again that interferometry could be used a device to 'filter' out substandard sections and that the critical threshold was set at the right level.

Immunohistochemistry

To illustrate the utility of the method, tissue and embedded cell line sections were immunohistochemically stained using the Oracle™ HER2 Bond™ IHC System (Leica Biosystems Newcastle Ltd) on an automated Bond-max system as follows:

1. On the Bond-max instrument, ensure the bulk and hazardous waste containers have enough capacity to perform the required staining runs.
2. Ensure there is adequate alcohol, distilled or de-ionized water, Bond Dewax Solution, Bond Epitope Retrieval Solution 1 and Bond Wash Solution (diluted to 1×) in the bulk reagent containers to perform the required staining runs.
3. Ensure that a clean Bond Mixing Station is installed.
4. Turn on the Bond-max fully automated, advanced staining system.
5. Turn on the PC attached to the Bond-max fully automated, advanced staining system.
6. Open the Bond software.
7. For a new Oracle HER2 Bond IHC System, scan the reagent tray barcodes with the handheld scanner to enter the system into the Bond reagent inventory.
8. Go to the Slide setup screen and click Add case.
9. Enter details for the first case. Ensure the dispense volume is set to 150 µL and the preparation protocol is *Dewax. Click OK.
10. With the case highlighted in the Slide setup screen click Add slide.
11. First, add patient test slides. Ensure tissue type is set to Test tissue.
12. Confirm the dispense volume is 150 µL and the preparation protocol is *Dewax.
13. Select staining mode values Single and Oracle (do not click Oracle control).
14. Select process IHC.
15. Select *HER2 Negative Control from the marker list. The Protocols tab defaults to the correct staining protocol (*IHC Protocol H) and HIER protocol (*HIER 25 min with ER1 (97)).
16. Click Add slide. The negative control reagent slide is created.
17. Still in the Add slide dialog, select *HER2 Primary Antibody from the marker list. Default protocols and all other settings remain unchanged.
18. Click Add slide. The test slide is created.
19. Repeat steps 8 to 18 until all cases and patient test slides have been created.
20. Next, create the HER2 Control Slide. Add it to the last case or create a new case for control slides, depending on your standard laboratory practices.
Important note: It is a requirement of the Oracle HER2 Bond IHC System that a HER2 Control Slide is included in each run (i.e. slide tray) in order to validate the assay.
21. In the Add slide dialog set tissue type to Positive tissue.
22. Click Oracle control.
23. Select the lot number of the HER2 Control Slide in the Lot No list. The lot number is inscribed on the label area of the slide. Important note: The HER2 Control Slide must come from the same Oracle HER2 Bond IHC System that will be used.
24. Select *HER2 Primary Antibody from the marker list. Retain dispense volume, staining mode, process and protocol settings.
25. Click Add slide to add the HER2 Control Slide.
26. Finally, add a positive in-house tissue control slide.
27. Deselect Oracle control.
28. Select *HER2 Primary Antibody from the marker list. Retain dispense volume, staining mode, and process and protocol settings. Tissue type remains Positive tissue.
29. Click Add slide. This completes slide creation.

30. Print slide labels. All Oracle slide labels have "OC" printed on them. The label for the HER2 Control Slide also includes the Oracle HER2 Bond IHC System lot number.
31. Label slides appropriately.
32. Open the lids of all Oracle HER2 Bond IHC System containers and load the reagent tray onto the Bond-max.
33. Place slides onto the slide tray in the order indicated in section D, Table 2. Apply new Covertiles.
34. Load the slide tray onto the Bond-max and press the Load/Unload button.
35. Confirm that the slides have been scanned and click the Run (Play) button on the System status screen.
36. Ensure that the tray indicator field displays Proc (OK) and batch number and finish time are displayed.
37. When the run is completed press the Load/Unload button and remove the slide trays from the Bondmax.
38. Remove Covertiles and rinse the slides in de-ionized water.
39. Dehydrate, clear and mount sections.

Example 2

Materials and Methods

Analysis of cell line section thickness was performed in three stages. For each stage, sections of control cells lines were cut from formalin fixed paraffin embedded (FFPE) blocks using a calibrated automated microtome (RM2255, Leica Microsystems). The blocks contained four FFPE cores: MDA-MB-231 (0) (European Collection of Cell Cultures—Catalogue No. 92020424), MDA-MB-175-VII (1+) (American Type Culture Collection—ATCC Catalogue No. HTB-25), MDA-MB-453 (2+) (ATCC, Catalogue No. HTB-131) and SK-BR-3 (3+) (ATCC, Catalogue No. HTB-30). The cell lines were grown using standard cell culture techniques, fixed in formalin, re-suspended in an agarose matrix and then processed on an automated Peloris (Leica Microsystems) tissue processor by dehydration in graded alcohols (70%, 90%, 100%) and cleared in xylene, before impregnation and embedding in paraffin wax.

The breast tumour tissue microarrays slides were purchased from Stretton Scientific, UK.

Stage 1. Testing to Investigate Relationship Between Interferometry and IHC Staining Profiles Forty (40) sections were sequentially cut from a composite cell block at eight microtome thickness settings, with five sections cut per setting (2.5, 3.0, 3.5, 4.0, 4.5, 5.0, 6.0 and 7.0 microns). Cut sections were placed onto pre-charged microscope slides (Leica Microsystems Plus slides, S21.2113). Slides were then incubated overnight at 37° C., followed by 2 hours at 60° C. The thickness of each cell spot in the section was measured by interferometry, and all slides were then assessed using the Oracle HER2 Bond IHC System (TA9145 Leica Microsystems).

Stage 2. Testing to Determine a 'Critical Thickness Threshold'

Ninety (90) sections were cut on a microtome set to 3 microns, measured by interferometry and then stained by IHC to determine if a 'critical threshold value' for the MDA-MB-453 (2+) cell line, the most critical cell line as identified in Stage 1 testing, could be used to filter acceptable from unacceptable control sections. Correlation of thickness versus HER2 protein expression for each cell line was performed.

Stage 3. Testing to Determine Suitability of the Critical Threshold

Seven hundred and seventy five (775) sections were cut at 3.0 microns. All sections were measured by interferometry. All sections that measured above the critical threshold value (see Results for Stage 2 testing) were 'rejected'. Sections in which the thickness measured below or equal to the critical threshold value were 'accepted'. All rejected sections and every 75$^{th}$ section of the remaining 'acceptable' slides were then stained by IHC to confirm suitability of the critical threshold.

Interferometer Measurements

Section thickness was determined for all slides using a Polytec TopMap white light interferometer with V2.1 software (Polytec). The interferometer was used to scan the area of the slide containing the cell lines, and changes in path length between waves of light, relative to the surface of the glass slide was assessed to determine a 'thickness' measurement in microns for each cell line. Additionally, tissue sections (n=3) were cut from a breast tumour tissue microarray that had previously been characterised for HER2 IHC staining (Stretton Scientific, UK), with the microtome set to 3.0, 5.0 and 7.0 microns. These sections were measured by interferometry and then stained by IHC using the method as described above.

Immunohistochemistry

All slides were stained using the Oracle HER2 Bond IHC System (Leica Microsystems, TA9145), on a Bond max automated staining platform (Leica Microsystems) according to the manufacture's instructions. HER2 scoring was conducted as recommended by the HER2 Testing in the United Kingdom—Further Update To recommendations (walker R. A. et al. *J. Clin. Pathol.*, Published on-line 2008).

Results

Stage 1.

An average thickness measurement was calculated for each group of five sections, and the values show that the interferometer measurement was consistently higher than the microtome setting. As the microtome thickness setting increased, variation in the difference between the measured interferometer thickness and the set thickness decreased. The effects of section thickness were not uniform across all cell lines (see Table 1), with the 2+ cell line appearing to be most sensitive to an increase in thickness, resulting in inappropriate staining. A borderline thickness area existed for the 3+ and 1+ cell lines in which cells were found to both pass and fail (see Table 3). Therefore, as a result of the 2+ cell line appearing most sensitive to variation in thickness, it was decided that it was only necessary to measure thickness of this cell line for Stage 2 testing. Interferometer readings could be obtained for 38/40 slides.

TABLE 1

Table 1: Summary of Stage 1 thickness measurements for each cell line, indicating differentiation into acceptable, unacceptable and borderline groups.

| Cell Line | Acceptable Thickness | Borderline Thickness | Unacceptable Thickness | Comments |
|---|---|---|---|---|
| SK-BR-3 (3+) | <4.2 μm (n = 13) | 4.2-5.1 μm (n = 9) | >5.1 μm (n = 16) | Unacceptable slides gave excessive membrane and cytoplasmic staining. The borderline thickness category includes sections that passed and failed. |

TABLE 1-continued

Table 1: Summary of Stage 1 thickness measurements for each cell line, indicating differentiation into acceptable, unacceptable and borderline groups.

| Cell Line | Acceptable Thickness | Borderline Thickness | Unacceptable Thickness | Comments |
|---|---|---|---|---|
| MDA-MB-453 (2+) | <3.5 μm (n = 8) | N/A | >3.8 μm (n = 30) | The MDA-MB-453 cell line was identified as the most critical of the four cell lines to be assessed for HER2 status, for which there was no borderline thickness region. |
| MDA-MB-175 (1+) | <3.5 μm (n = 7) | 3.5-4.5 μm (n = 11) | >4.8 μm (n = 20) | Failure with this cell line was associated with complete membrane staining in some cells and an increase in cytoplasmic staining. |
| MDA-MB-231 (0) | <8.5 μm (n = 38) | N/A | N/A | Interpretation of staining in the negative cell line was unaffected by section thickness |

Stage 2.

Sections failed IHC when the 2+ cell spot measured above 3.28 μM due to excessive membrane and cytoplasmic staining, except for four sections measuring 3.33, 3.35, 3.36 and 3.43 μm. These four passes indicate that a borderline thickness exists between 3.28 and 3.43 μm. Therefore, a conservative 'Critical Threshold Value' for the MDA-MB-453 (2+) cell line of 3.25 μm was adopted for use in Stage 3 testing.

Stage 3.

From a total of 775 slides, 144 sections were found to measure above the critical threshold of 3.25 μm as established for the 2+ cell line. Furthermore, when stained by IHC, 132 out of 144 (92%) of these same slides failed to meet the staining requirements as visualised using the Oracle HER2 Bond IHC System. Furthermore, HER2 IHC staining of every $75^{th}$ section, from the remaining 631 sections (<3.25 μm), showed that all sections (100%, n=8) had acceptable IHC results.

Effects of Tissue Section Thickness on HER2 Interpretation

The effects of section thickness was analysed using a breast tumour tissue microarray (TMA) containing 20 separate breast tumours previously characterised for HER2 expression. When sectioned between 3 and 5 HER2 expression in the TMA varied in core F2 from 0 to 1+. In a diagnostic setting, both of these scores would have been classed as clinically negative for HER2 staining. When sectioned at 7 μm there was an increase in the HER2 profile of four samples, with two of these, A1 and A2, changing their HER2 profile from a negative (1+) to a positive borderline (2+) result. The remaining 16 cores showed no change in HER2 expression as thickness increased.

Additional Observations

Individual control cell line spots varied in thickness, often exhibiting a raised profile towards the outer edge of the core, with a central depression. This phenomenon was observed for all cell lines and was evident in the vast majority of cell line sections but was not evident in tissue.

The claim defining the invention are as follows:

1. A method of preparing a cell line sample for use as a control sample in HER2 testing, said method comprising:
   (i) mounting a sectioned MDA-MB-453 cell line sample onto a planar support;
   (ii) measuring the thickness of the cell line sample using an interferometer; and
   (iii) selecting the sample for use as a 2+ control if the thickness of the sectioned cell line sample is in the range of 2.20-3.28 μm.

2. The method according to claim 1, wherein the sectioned sample is a section of cells derived from a cultured cell line or a cell block.

3. The method according to claim 2, wherein the sectioned sample is a section of cells derived from a cultured cell line embedded in a rigid support medium.

4. The method according to claim 3, wherein the sample is a formalin-fixed, paraffin-embedded sample.

5. The method according to claim 1, wherein the sectioned sample further comprises 0, 1, 2, or 3 additional cell lines.

6. The method according to claim 1, wherein the sectioned sample further comprises at least one cell line selected from: a 0 cell line, a 1+ cell line, and a 3+ cell line.

7. The method according to claim 6, wherein:
   the 0 cell line sample is selected from MDA-MB-231 and MDA-MB-468;
   the 1+ cell line sample is selected from MDA-MB-175, BT-549, MCF-7, and T47D; and
   the 3+ cell line sample is selected from SKBR3, BT-474, and SKOV-3.

8. The method according to claim 6, wherein:
   the 0 cell line sample is MDA-MB-231;
   the 1+ cell line sample is MDA-MB-175; and
   the 3+ cell line sample is selected from SKBR3.

9. The method according to claim 6, further comprising measuring the thickness of the at least one sectioned 0, 1+ or 3+ cell line sample using an interferometer, and
   Selecting the sample for use as a 0 control if the thickness of the sectioned 0 cell line sample is in the range of 2.0-8.5 μm; and/or
   selecting the sample for use as a 1+ control if the thickness of the sectioned 1+ cell line sample is in the range of 2.2-3.5 μm; and/or
   selecting the sample for use as a 3+ control if the thickness of the sectioned 3+ cell line sample is in the range of 2.5-4.2 μm.

10. The method according to claim 1, wherein the sectioned sample further comprises at least two cell lines selected from: a 0 cell line, a 1+ cell line, and a 3+ cell line.

11. The method according to claim 1, wherein the sectioned sample further comprises a 0 cell line, a 1+ cell line, and a 3+ cell line.

12. The method according to claim 1, further comprising mounting at least one additional cell line sample section onto a planar support, wherein said cell line sample is selected from a 0 cell line sample, a 1+ cell line sample, and a 3+ cell line sample.

13. The method according to claim 12, wherein:
   the 0 cell line sample is selected from MDA-MB-231 and MDA-MB-468;
   the 1+ cell line sample is selected from MDA-MB-175, BT-549, MCF-7, and T47D; and the 3+ cell line sample is selected from SKBR3, BT-474, and SKOV-3.

14. The method according to claim 12, wherein:
the 0 cell line sample is MDA-MB-231;
the 1+ cell line sample is MDA-MB-175; and
the 3+ cell line sample is SKBR3.

15. The method according to claim 12, further comprising measuring the thickness of the at least one 0, 1+, or 3+ cell line sample section using an interferometer; and
  selecting the sample for use as a 0 control if the thickness of the sectioned 0 cell line sample is in the range of 2.0-8.5 µm; and/or
  selecting the sample for use as a 1+ control if the thickness of the sectioned 1+ cell line sample is in the range of 2.2-3.5 µm;
  and/or selecting the sample for use as a 3+ control if the thickness of the sectioned 3+ cell line sample is in the range of 2.5-4.2 µm.

* * * * *